(12) United States Patent
Moussa

(10) Patent No.: US 9,649,204 B2
(45) Date of Patent: May 16, 2017

(54) MEDICAL IMPLANT AND KNEE JOINT ENDOPROSTHESIS

(71) Applicant: Aesculap AG, Tuttlingen (DE)

(72) Inventor: Saïd Moussa, Chamarandes-Choignes (FR)

(73) Assignee: Aesculap AG, Tuttlingen (DE)

( * ) Notice: Subject to any disclaimer, the term of this patent is extended or adjusted under 35 U.S.C. 154(b) by 198 days.

(21) Appl. No.: 14/702,826

(22) Filed: May 4, 2015

(65) Prior Publication Data

US 2015/0297359 A1 Oct. 22, 2015
US 2017/0071760 A9 Mar. 16, 2017

Related U.S. Application Data

(63) Continuation of application No. 12/807,455, filed on Sep. 2, 2010, now Pat. No. 9,044,328, which is a continuation of application No. PCT/EP2009/052477, filed on Mar. 2, 2009.

(30) Foreign Application Priority Data

Mar. 7, 2008 (DE) ........................ 10 2008 014 837

(51) Int. Cl.
*A61F 2/46* (2006.01)
*A61F 2/38* (2006.01)
*A61F 2/30* (2006.01)

(52) U.S. Cl.
CPC ............ *A61F 2/4637* (2013.01); *A61F 2/389* (2013.01); *A61F 2002/3049* (2013.01); *A61F 2002/30504* (2013.01); *A61F 2002/30512* (2013.01); *A61F 2002/30878* (2013.01)

(58) Field of Classification Search
CPC ....................................................... A61F 2/46
See application file for complete search history.

(56) References Cited

U.S. PATENT DOCUMENTS

| | | | |
|---|---|---|---|
| 4,822,366 A | 4/1989 | Bolesky | |
| 4,985,037 A | 1/1991 | Petersen | |
| 5,061,271 A | 10/1991 | Van Zile | |
| 5,133,760 A | 7/1992 | Petersen et al. | |
| 5,152,796 A | 10/1992 | Slamin | |
| 5,290,313 A | 3/1994 | Heldreth | |
| 5,326,359 A | 7/1994 | Oudard | |

(Continued)

FOREIGN PATENT DOCUMENTS

| | | |
|---|---|---|
| DE | 697 29 608 | 7/2005 |
| DE | 699 18 894 | 8/2005 |

(Continued)

*Primary Examiner* — Matthew Schall
(74) *Attorney, Agent, or Firm* — Lipsitz & McAllister, LLC

(57) ABSTRACT

The invention relates to a medical implant consisting of a first implant part and a second implant part for the connection of which there is provided a connecting device, wherein at least the first implant part comprises a connecting element receptacle, in which at least one connecting element of the connecting device can be disposed. In order to provide an implant of this type which is easier to handle, it is proposed, in accordance with the invention, that a securing device be provided for the purposes of securing the at least one connecting element in the connecting element receptacle. Moreover, the invention relates to a knee joint endoprosthesis having at least one implant of this type.

20 Claims, 3 Drawing Sheets

(56) References Cited

U.S. PATENT DOCUMENTS

| | | | |
|---|---|---|---|
| 5,330,535 A | 7/1994 | Moser et al. |
| 5,556,433 A | 9/1996 | Gabriel et al. |
| 5,683,472 A | 11/1997 | O'Neil et al. |
| 5,782,920 A | 7/1998 | Colleran |
| 5,782,921 A | 7/1998 | Colleran et al. |
| 5,824,097 A | 10/1998 | Gabriel et al. |
| 5,879,391 A | 3/1999 | Slamin |
| 5,944,756 A | 8/1999 | Fischetti et al. |
| 6,063,122 A | 5/2000 | O'Neil et al. |
| 6,071,311 A | 6/2000 | O'Neil et al. |
| 6,086,614 A | 7/2000 | Mumme |
| 6,126,693 A | 10/2000 | O'Neil et al. |
| 6,146,424 A | 11/2000 | Gray, Jr. et al. |
| 6,162,255 A | 12/2000 | Oyola |
| 6,171,342 B1 | 1/2001 | O'Neil et al. |
| 6,214,052 B1 | 4/2001 | Burkinshaw |
| 6,423,096 B1 | 7/2002 | Musset et al. |
| 6,436,145 B1 | 8/2002 | Miller |
| 6,506,216 B1 | 1/2003 | McCue et al. |
| 6,527,807 B1 | 3/2003 | O'Neil et al. |
| 6,620,168 B1 | 9/2003 | Lombardo et al. |
| 6,699,290 B1 | 3/2004 | Wack et al. |
| 6,869,447 B2 | 3/2005 | Lee et al. |
| 6,923,832 B1 | 8/2005 | Sharkey et al. |
| 6,953,479 B2 | 10/2005 | Carson et al. |
| 7,025,788 B2 | 4/2006 | Metzger et al. |
| 7,153,326 B1 | 12/2006 | Metzger |
| 8,540,775 B2 | 9/2013 | Reich et al. |
| 2002/0120340 A1 | 8/2002 | Metzger et al. |
| 2002/0120341 A1 | 8/2002 | Stumpo et al. |
| 2003/0014120 A1 | 1/2003 | Carson et al. |
| 2003/0055508 A1 | 3/2003 | Metzger et al. |
| 2003/0055509 A1 | 3/2003 | McCue et al. |
| 2003/0204264 A1 | 10/2003 | Stumpo et al. |
| 2004/0049286 A1 | 3/2004 | German et al. |
| 2005/0154470 A1 | 7/2005 | Sekel |
| 2006/0030945 A1 | 2/2006 | Wright |
| 2007/0150065 A1 | 6/2007 | Angibaud |
| 2008/0306603 A1 | 12/2008 | Reich et al. |

FOREIGN PATENT DOCUMENTS

| | | |
|---|---|---|
| DE | 20 2007 008 538 | 9/2007 |
| EP | 0 502 815 | 9/1992 |
| EP | 0 376 658 | 6/1994 |
| EP | 0 545 833 | 4/1997 |
| EP | 0 947 181 | 10/1999 |
| EP | 0 980 679 | 2/2000 |
| EP | 0 985 386 | 3/2000 |
| EP | 0 986 994 | 3/2000 |
| EP | 0 993 813 | 4/2000 |
| EP | 0 714 645 | 5/2000 |
| EP | 0 853 930 | 7/2002 |
| EP | 1 234 557 | 8/2002 |
| EP | 0 781 535 | 5/2003 |
| EP | 0 820 739 | 6/2004 |
| EP | 0 956 836 | 7/2004 |
| EP | 0 966 928 | 9/2005 |
| EP | 1 623 686 | 2/2006 |
| WO | WO 03/007852 | 1/2003 |
| WO | WO 03/065939 | 8/2003 |
| WO | WO 2007/114841 | 10/2007 |

MEDICAL IMPLANT AND KNEE JOINT ENDOPROSTHESIS

This application is a continuation of U.S. application Ser. No. 12/807,455 filed on Sep. 2, 2010, which is a continuation of international application number PCT/EP2009/052477 filed on Mar. 2, 2009 and which claims the benefit of German Patent Application No. 10 2008 014 837.7 filed on Mar. 7, 2008, each of which are incorporated herein by reference in their entirety and for all purposes.

FIELD OF THE INVENTION

The invention relates to a medical implant comprising a first implant part and a second implant part, for the connection of which there is provided a connecting device, wherein at least the first implant part has a connecting element receptacle in which at least one connecting element of the connecting device is disposable.

Moreover, the invention relates to a knee joint endoprosthesis comprising at least one implant having a first implant part and a second implant part, for the connection of which there is provided a connecting device, wherein at least the first implant part comprises a connecting element receptacle in which at least one connecting element of the connecting device is disposable.

BACKGROUND OF THE INVENTION

For the purposes of connecting the first implant part to the second implant part, the connecting device comprises at least one connecting element which can be disposed in the connecting element receptacle of the first implant part. This first connecting element of the connecting device can, for example, cooperate with a second connecting element of the connecting device which is disposed or can be disposed on the second implant part for example.

An implant of this generic type is described in DE 20 2007 008 538 U1 and comprises a first implant part which defines a tibia plateau and partially comprises a connecting device and also comprises a second implant part in the form of a tibia shaft. The connecting device comprises a groove-shaped connecting element receptacle into which a first connecting element in the form of a nut can be inserted and then screwed to a second connecting element in the form of a threaded spindle which is arranged on the tibia shaft in order to connect the two implant parts with each other.

The object of the present invention is to provide an implant of the above generic type and also a knee joint endoprosthesis of the above generic type which is easier to handle.

SUMMARY OF THE INVENTION

In accordance with the invention, this object is achieved in the case of an implant of the type specified at the outset in that a securing device is provided for securing the at least one connecting element in the connecting element receptacle.

BRIEF DESCRIPTION OF THE DRAWINGS

The foregoing summary and the following description of preferred embodiments of the invention serve to provide a more detailed explanation of the invention taken in conjunction with the drawing of which.

DETAILED DESCRIPTION OF THE INVENTION

Figure 1:
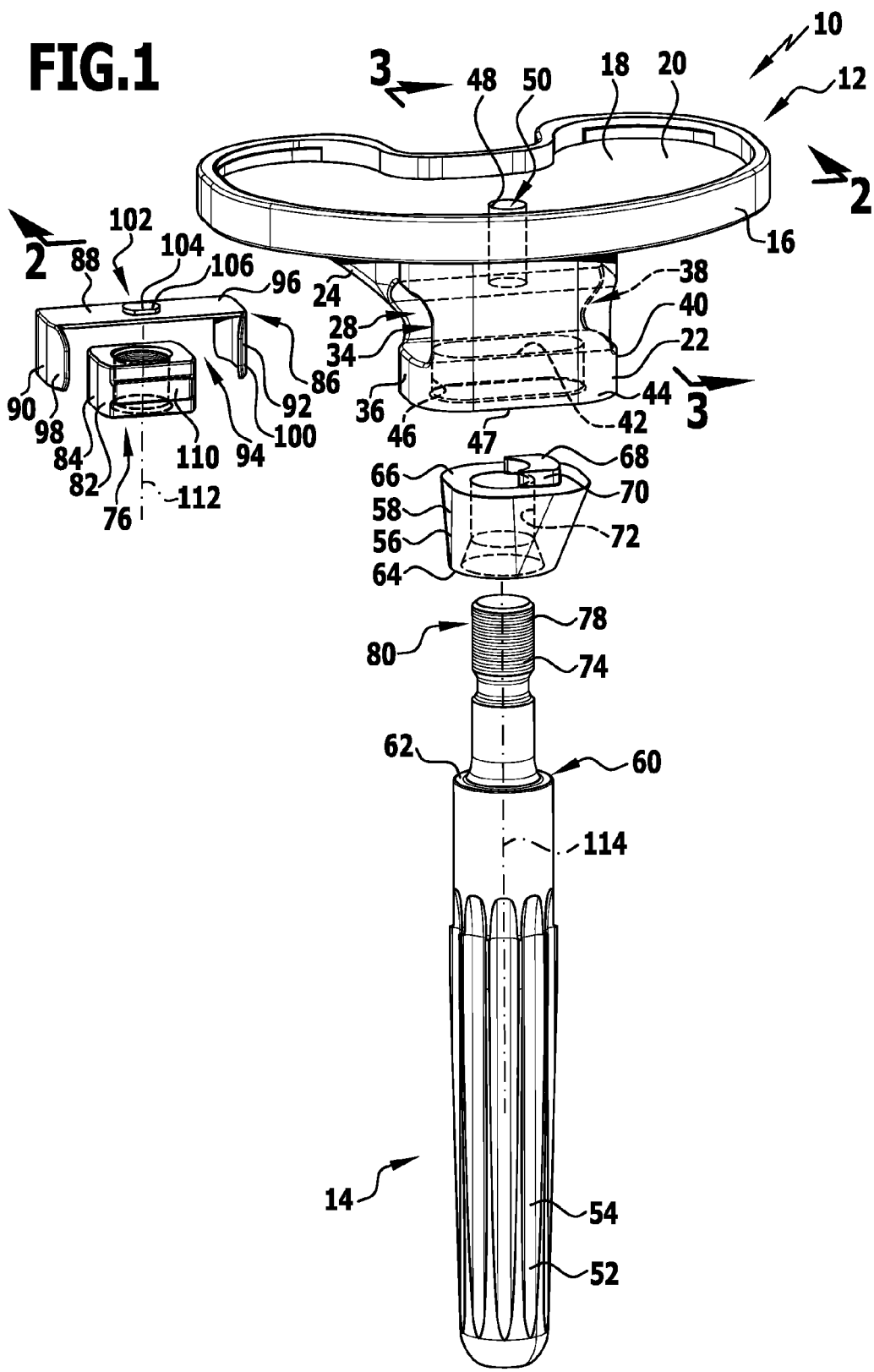
FIG. 1: shows a perspective exploded illustration of a medical implant in accordance with the invention.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical implant comprising a first implant part and a second implant part, for the connection of which there is provided a connecting device, at least the first implant part comprising a connecting element receptacle, in which at least one connecting element of the connecting device is disposable, wherein a securing device is provided for securing the at least one connecting element in the connecting element receptacle.

The at least one connecting element can be secured in the connecting element receptacle by means of the securing device. This thus prevents the at least one connecting element from being unintentionally released from the connecting element receptacle, for example, from being moved out of it. This results in improved handling of the implant. Thus, for example, prior to the connection of the first implant part to the second implant part, the at least one connecting element can be inserted into the connecting element receptacle and then secured therein with the aid of the securing device which, for example, may adopt a secured position for this purpose. Consequently, a user can pay proper attention to the process of connecting the first implant part to the second implant part without having to additionally concern himself with securing the at least one connecting element in the connecting element receptacle. Once the first implant part has been connected to the second implant part, the securing of the at least one connecting element in the connecting element receptacle can have a positive effect upon the reliability of the connection of the two implant parts. The securing process can be ensured for example by the use of a means for holding the at least one connecting element in the connecting element receptacle, wherein a "holding means" is to be understood as meaning both a fixed form of mounting and a moveable one.

It is expedient if the securing device is arranged on the first implant part and/or is comprised thereby because this then allows a compact construction of the implant to be achieved.

It is of advantage for the securing device to be arranged on the connecting device and/or to be comprised thereby whereby provision may be made, in particular, for the securing device to be arranged on the at least one connecting element and/or to be comprised thereby. A compact construction of the implant can also be obtained in this way.

Preferably, there is associated with the at least one connecting element an abutment member upon which the connecting element is placeable for inserting it into the connecting element receptacle. This makes it easier for a user to insert the at least one connecting element into the connecting element receptacle and thereby improves handling of the implant. The abutment member can, for example, form an abutment surface for the at least one connecting element upon which the latter can be placed for inserting it into the connecting element receptacle. Provision may also be made for the at least one connecting element lying on the abutment member to be inserted together therewith into the connecting element receptacle.

In order to obtain a compact construction for the implant, the securing device preferably comprises the at least one abutment member.

It is preferred that the securing device should comprise at least one securing member for securing the at least one connecting element in the connecting element receptacle, for example, in a secured position of the securing device. It is expedient for the purposes of achieving a compact construction of the implant, that the at least one securing member be arranged on the first implant part and/or on the connecting device, whereby in particular, it can be arranged on the at least one connecting element.

It is of advantage for the connecting element receptacle to have at least one insertion opening for the at least one connecting element, whereby said insertion opening is at least partially closeable by the at least one securing member. This gives rise to the possibility of securing the at least one connecting element in the connecting element receptacle in a technically simple manner. The insertion opening can be at least partially closed by means of said at least one securing member so that the residual cross-sectional area thereof will be smaller than the cross-sectional area of the at least one connecting element whereby the latter cannot be moved out of the connecting element receptacle.

It is particularly expedient for the at least one insertion opening to be completely or substantially completely closeable by means of the at least one securing member. This permits the at least one connecting element to be secured yet more reliably in the connecting element receptacle.

Preferably, the at least one insertion opening is formed in a wall section of the first implant part, and the at least one securing member is substantially flush with the wall section or at least portions thereof are flush with the wall section, for example, when the securing device is in its secured position. This permits a smooth transition from the wall section to the at least one securing member to be obtained. These can thus form a common surface, whereby the at least one securing member is fitted into the insertion opening in such a manner that there is preferably no joining gap therebetween or substantially no joining gap therebetween. In consequence, not only can the at least one connecting element be reliably secured in the connecting element receptacle, but it also gives rise to the possibility that material located outside the connecting element receptacle cannot penetrate into the connecting element receptacle at all or that there is only a small probability of such penetration. Such material is, for example, bone cement which is utilised for fixing the implant in the body of a patient. Moreover, due to the flush or substantially flush transition between the wall section and the at least one securing member, undercuts in the vicinity of the at least one insertion opening in which bone cement could undesirably accumulate can be prevented.

It is of advantage for the connecting element receptacle to comprise two insertion openings for the insertion of the at least one connecting element and for the securing device to have two securing members with which a respective insertion opening is closeable at least in sections thereof, and still more advantageously, if the opening is completely or substantially completely closeable. The presence of two insertion openings makes it easier for a user to insert the at least one connecting element into the connecting element receptacle. Depending upon the accessibility of the implant during an operation, one or other of the insertion openings can prove to be better suited for inserting the at least one connecting element. In order to include as large a solid angle as possible, it is expedient for the two insertion openings to be formed on mutually opposite sides of the connecting element receptacle.

The two securing members are preferably connected to one another. This permits the securing device to be of technically simple construction since separate securing members which could possibly get lost do not have to be provided. Instead, the two securing members are connected together and in particular, it is possible for the securing device to be formed in one-piece manner. Preferably, the connection of the two securing members to one another can be effected with the aid of the previously described abutment member of the securing device upon which the at least one connecting element is placeable for inserting it into the connecting element receptacle.

A simple construction of the securing device can be obtained if the securing device is symmetrical on the basis that at least the two securing members are formed such that they are mutually symmetrical, whereby it is still more expedient for the entire securing device to be formed symmetrically. Moreover, it is of advantage in this embodiment if the connecting element receptacle is likewise formed symmetrically. In consequence, the effect can be achieved that each insertion opening can be closed to at least a partial extent by each of the two securing members. The process of handling the implant is thereby improved.

Preferably, the securing device forms a securing receptacle for the at least one connecting element which is at least partly bounded by one or more walls. Apart from the connecting element receptacle, the at least one connecting element can be arranged in the securing receptacle and secured therein in order to introduce it into the connecting element receptacle for example. To this end, the at least one connecting element can be placed at the one or more walls of the securing device for example.

It is particularly expedient if at least one of the one or more walls of the securing device bounds the connecting element receptacle, at least in sections thereof. In this way, the one or more walls have a double function because they at least partly bound both the securing receptacle and the connecting element receptacle. It is particularly preferred that such a wall be the previously described at least one securing member of the securing device.

Provision may be made for the at least one connecting element to be arranged moveably in the securing receptacle, and in particular, for it to be mounted in moveable manner. This permits the at least one connecting element to be secured to the first implant part in moveable manner, this thereby giving rise to the possibility of the at least one connecting element being able to adopt a plurality of positions relative to the second implant part. This can be of advantage when inserting the implant into the body of a patient in order to adapt the orientation of the two implant parts relative to one another to the needs of the particular patient.

The implant can be handled in a particularly simple way if the securing device is transferable from an assembly position, in which the at least one connecting element can be inserted into the connecting element receptacle, into a secured position in which the at least one connecting element is secured in the connecting element receptacle by means of the securing device. In order to achieve the same advantage, provision may also be made for the previously described at least one securing member alone to be transferable from such an assembly position into such a secured position.

It is expedient if the securing device is mounted on the first implant part such that it is at least partially moveable for transferring it from the assembly position into the secured position because this makes it easier for a user to handle the securing device.

Preferably, the securing device can be inserted into the connecting element receptacle to at least a partial extent for transferring it from the assembly position into the secured position. When in the assembly position, the securing device can be arranged partly or entirely outside the connecting element receptacle and, in this way, the latter can make free an insertion opening for the insertion of the at least one connecting element and/or the securing device. In this embodiment, the securing device preferably comprises the previously described abutment member and the previously described at least one securing member so that the at least one connecting element can rest on the abutment member for inserting it into the connecting element receptacle and can then be inserted into the connecting element receptacle by transferring the securing device from the assembly position into the secured position. The aforesaid insertion opening can be closed for example by means of the previously described at least one securing member. Thus, to a certain extent, a securing device of this type has the function of a "drawer" for the at least one connecting element and it can be handled in a particularly simple manner by a user.

Advantageously, the securing device can be inserted into the connecting element receptacle in its entirety, whereby it does not protrude beyond the outer boundaries of the first implant part when in the secured position. This permits the implant to be provided with a compact construction. Moreover, this gives rise to the possibility of preventing subsequent manipulation of the securing device when it is in the secured position. Then, due to the fact that it does not protrude beyond the outer boundaries of the implant part, a user has very little to grip hold of in order to possibly remove it from the secured position.

It is expedient if the first implant part defines a guidance means for the securing device because the latter can then be transferred from the assembly position into the secured position in this way without a user needing to direct special attention to the movement of the securing device whilst so doing.

For example, provision may be made for the securing device to be guided in slidable manner by the first implant part, for example, in the case where the securing device is insertable at least partially into the connecting element receptacle for the transfer from the assembly position into the secured position.

It is of advantage for the securing device to be retained in the connecting element receptacle in force—and/or positively-locking manner when it is in the secured position. This then ensures that the at least one connecting element is reliably secured in the connecting element receptacle.

In order to retain the securing device in the connecting element receptacle in force—and/or positively-locking manner, it is expedient if the securing device has a locking device for locking the securing device in the secured position. This thus gives rise, in particular, to the possibility of configuring the implant in such a way that the securing device is transferable from the assembly position into the secured position once, whereafter it can no longer return from the secured position to the assembly position.

In the case of one constructionally simple implementation of the implant, the locking device advantageously comprises at least one locking member which is in engagement with the first implant part in the secured position of the securing device. Such engagement between the at least one locking member and the first implant part can be in the form of a force—and/or positively-locking coupling for example.

The securing device is adapted to be locked in the connecting element receptacle by means of the locking device in a particularly reliable manner, if the securing device can be inserted into the connecting element receptacle in a direction which is orientated transversely and in particular, perpendicularly with respect to the direction of engagement of the at least one locking member and the first implant part, and/or, transversely with respect to the effective direction of engagement. It is yet more preferable if the direction of insertion of the securing device is orientated perpendicularly with respect to the direction of engagement and/or the effective direction thereof.

The securing device can be produced in a constructionally simple manner, if the at least one locking member is in the form of a projection or a receptacle which respectively cooperates with a correspondingly formed receptacle or a correspondingly formed projection of the first implant part.

The implant is particularly easy to handle, if the at least one locking member is in the form of a latching element, for example, a latching projection or a latching receptacle.

Advantageously, the at least one connecting element is mounted in the connecting element receptacle in moveable manner. This gives rise to the possibility that the at least one connecting element can adopt a plurality of positions relative to the first and/or the second implant part, this being useful during the process of orientating the two implant parts relative to one another. The at least one connecting element can adopt a plurality of discrete positions for example. In addition or as an alternative thereto, it can be mounted in the connecting element receptacle in such a way that it is adjustable relative thereto and also relative to the first and/or second implant part in stepless manner. In this embodiment, the two implant parts can thus be orientated relative to each other in accord with the needs of the patient when inserting the implant into the patient's body for example.

In particular, provision may be made for the at least one connecting element to be mounted in the connecting element receptacle in slidable manner.

In order to enable the at least one connecting element to move reliably in the connecting element receptacle, the first implant part preferably defines a guidance means for the at least one connecting element which is arranged in the connecting element receptacle.

Advantageously, the at least one connecting element comprises at least one rotation-preventing member for forming a means for preventing the at least one connecting element from rotation relative to the connecting element receptacle. This, for example, gives rise to the possibility of maintaining the orientation of the at least one connecting element relative to the second implant part or of obtaining such orientation in the first place. This makes it easier for a user to connect the implant parts to one another. For the purposes of preventing rotation for example, the at least one connecting element can be arranged in positively-locking manner between walls of the first implant part which at least partially bound the connecting element receptacle.

The at least one rotation-preventing member may, for example, be in the form of a projection from the at least one connecting element which abuts a wall of the first implant part which at least partially bounds the connecting element receptacle, or else is in engagement with this wall.

It is also possible for the at least one rotation-preventing member to be formed by a side face of the connecting element which abuts a wall of the first implant part that at least partially bounds the connecting element receptacle for example.

It is of advantage, if the connecting element receptacle comprises at least one engagement opening for at least one connecting element which is disposed on or which is disposable on the second implant part. In this way, the at least one connecting element which is disposed on or can be disposed on the second implant part can be passed through the at least one engagement opening in order to bring it into engagement with the at least one connecting element of the first implant part for example.

The at least one engagement opening can be produced in a constructionally simple manner by forming said at least one engagement opening as a through hole in a wall region of the first implant part.

Here, it is expedient if the wall region forms an abutment surface for the second implant. In particular, the wall region may form an abutment flange for the second implant part. In consequence, the second implant part can adopt a defined position relative to the first implant part, this not only making it easier for a user to handle the implant, but it is also suitable for ensuring long term retention of a defined relative orientation of the two implant parts after the implant has been inserted into the body of a patient.

Preferably, the through hole defines an elongate hole which is orientated transversely and in particular, perpendicularly relative to an axis of the at least one connecting element. The at least one connecting element can be connected along its axis to a connecting element of the second implant part for example. If the at least one connecting element is arranged in the connecting element receptacle in moveable manner, such that it is slidable in the direction of extent of the elongate hole for example, then the first implant part and the second implant part can be moved, and in particular displaced, relative to one another.

As mentioned hereinabove, the invention also relates to a knee joint endoprosthesis. In the case of a knee joint endoprosthesis of the above generic type, the object specified above is achieved in accordance with the invention in that a securing device is provided for securing the at least one connecting element in the connecting element receptacle.

The knee joint endoprosthesis in accordance with the invention then exhibits the advantages that have already been mentioned in connection with the explanation of the implant in accordance with the invention.

Expediently, the at least one implant of the knee joint endoprosthesis is formed in the manner of one of the preceding implants. The knee joint endoprosthesis then exhibits the further advantages that were mentioned in the explanation of these implants.

The first implant part of the at least one implant of the knee joint endoprosthesis can, for example, form a tibia part and the second implant part a tibia shaft so that the at least one implant can form the tibia-side part of the knee joint endoprosthesis.

It is also possible for the first implant part to form a femur part of the knee joint endoprosthesis and for the second implant part to form a femur shaft so that the at least one implant can form the femur-side part of the knee joint endoprosthesis.

A preferred embodiment of an implant in accordance with the invention is marked with the reference symbol 10 in the drawing. The implant 10 forms the tibia-side part of a knee joint endoprosthesis and, for this purpose, it comprises a first implant part 12 and also a second implant part 14. The first implant part 12 forms a so-called tibia part which is used at the proximal end of a patient's tibia. For the purposes of forming the implant 10, the latter part can cooperate, as will be described below, with the second implant part 14 which forms a so-called tibia shaft. The second implant part 14 is inserted into the tibia at the distal end relative to the first implant part 12.

Apart from "proximal" and "distal", use will also be made hereinafter of other positional and directional indications in the reference system of a patient's body that are in common use by the skilled person.

The implant part 12 comprises a head part 16 including a supporting section 18 which forms a bearing surface 20 for the meniscus part of a knee joint endoprosthesis, this part not being shown in the drawing since it is known. In a known manner that is not shown in the drawing, the meniscus part can cooperate with a likewise known and not shown femur part of the knee joint endoprosthesis.

Projecting from the supporting section 18 in the distal direction, there is an anchorage section 22 which can be inserted into a previously prepared recess at the proximal end of the tibia of a patient. The anchorage section 22 is connected to the supporting section 18 in one-piece manner. In plan view, it is approximately in the form of a rectangle with rounded off corners and at the sides thereof, there are two reinforcement sections 24 and 26 which project towards the supporting section 18.

At a point approximately half way along the extent of the anchorage section 22 in the distal direction, it has a receptacle which is referred to hereinafter as a connecting element receptacle 28 and which is oriented perpendicularly relative to the proximal-distal direction and runs in the lateral-medial direction. It is partially bounded in the proximal direction by a top wall 30 and in the distal direction by a bottom wall 31 which are each of flat formation and thereby define planes that run in parallel with the plane defined by the bearing surface 20. In the posterior and anterior directions, the connecting element receptacle 28 is respectively bounded by a side wall 32 and a side wall 33 which connect the top wall 30 and the bottom wall 31 together.

A first opening of the connecting element receptacle 28 which is referred to hereinafter as the first insertion opening 34 is formed in a lateral wall section 36 of the anchorage section 22, and a second opening, which is referred to hereinafter as the second insertion opening 38 of the connecting element receptacle 28, is formed in a medial wall section 40 of the anchorage section 22.

A through hole 42 which extends from the bottom wall 31 of the connecting element receptacle 28 in the distal direction is formed in a wall region 44 at the distal end of the anchorage section 22. Furthermore, the through hole 42 is extended in parallel with the connecting element receptacle 28 from the lateral side to the medial side and thereby defines an elongate hole 46. The wall region 44 is of flat formation and defines an abutment surface 47 for the second implant part 14.

A further through hole 48 in the form of a cylindrical bore 50 in the head part 16 extends between the top wall 30 and the bearing surface 20.

The head part 16 is symmetrical with respect to a plane from the posterior to the anterior which is perpendicular to the plane defined by the bearing surface 20 and runs through the centre of the bore 50.

The second implant part 14 which is to be connected to the first implant part 12 is formed in two-piece manner and comprises an anchorage part 52 in the form of a shaft 54 and also an adapter part 56 in the form of a collar 58 which can be placed on said shaft. When inserting the implant 10 into the body of a patient, the shaft 54 has to be inserted into a previously prepared recess in the tibia and then forms the distal end of the implant 10. Near the upper end thereof, the shaft has a peripheral ring-like shoulder 60 which defines an abutment surface 62 for a corresponding distal abutment surface 64 that is formed on the collar 58 and is likewise formed in ring-like manner.

An abutment surface 66, which is formed in corresponding manner to the abutment surface 47 on the head part 16, is formed at the proximal end of the collar 58. A rotation-preventing member 68 in the form of a projection 70 protruding from the abutment surface 66 in the proximal direction is arranged on the abutment surface 66, whereby said member can project into the through hole 42 where it is flush with the wall thereof. The head part 16 and the collar 58 are thus prevented from rotation relative to one another in this way, the collar 58 being able to move relative to the head part 16 along the abutment surface 47 in the lateral-medial direction as is symbolized in FIG. 2 by a double arrow, insofar as the collar 58 is not fixed to the head part 16 as is to be described hereinbelow.

When inserting the implant 10, the proximal end of the shaft 54 is passed through a through hole 72 in the collar 58 and also through the through hole 42 in the head part 16 so as to engage into the connecting element receptacle 28. Thus, in this way, the shaft 54 is also displaceable relative to the head part 16.

The proximal end of the shaft 54 forms a connecting element 74 for a connecting device 76 of the implant 10 which is provided for the purposes of interconnecting the implant part 12 and the implant part 14. Here, the connecting element 74 is arranged to be in the form of a threaded section 78 having an externally located thread 80. The dimensions of the threaded section 78 are such as to allow approximately three quarters thereof to engage in the connecting element receptacle 28.

For the purposes of connecting it to the second implant part 14, the first implant part 12 comprises a connecting element 82 which is a component of the connecting device 76 in like manner to the connecting element 74. The connecting element 82 is in the form of a nut 84 which is insertable into the connecting element receptacle 28 where it can be connected to the threaded section 78 by a screwing action.

In order to secure the nut 84 in the connecting element receptacle 28, i.e. to retain it therein and in particular to retain it in moveable manner therein, the implant 10 in accordance with the invention and in particular the first implant part 12 thereof comprises a securing device 86 which will be described hereinafter.

The securing device 86 comprises a longitudinally-extended element 88 which defines a plane and from the ends whereof two curved walls 90 and 92 project perpendicularly relative to the plane. The securing device 86 is thus in the form of a clamping configuration. Taken as a whole, it is symmetrical, whereby the walls 90 and 92 are mutually symmetrical taken with reference to a plane of symmetry which is perpendicular to the plane defined by the element 88.

Between the element 88 and the walls 90 and 92, there is defined a securing receptacle 94 for the nut 84 into which the nut 84 can be inserted in a simple manner since the securing receptacle 94 is not bounded at the side opposite the element 88. The nut 84 can be placed in the securing receptacle 94 for inserting it into the connecting element receptacle 28, this insertion process being effected with the help of the securing device 86. To this end, the nut 84 can be placed on the element 88 so that the latter defines an abutment member 96 of the securing device 86. The placing of the nut 84 on the element 88 is helpful for inserting the nut 84 into the connecting element receptacle 28 but it is not absolutely essential therefor. It suffices for the nut 84 to be arranged in the securing receptacle 94 in such a way that both the securing device 86 and the nut 84 can be inserted into the connecting element receptacle 28 through one of the insertion openings 34 or 38.

Due to the previously described design thereof, the securing device 86 forms a sort of "drawer" for the nut 84 for inserting it into the connecting element receptacle 28. It is thereby transferable from an assembly position in which the nut 84 is insertable into the connecting element receptacle 28—i.e. at least one of the insertion openings 34 or 38 is freely accessible—into a secured position in which the nut 84 is secured, and in particular, retained in the connecting element receptacle 28.

The process of inserting the securing device 86 together with the nut 84 into the connecting element receptacle 28, i.e. the transference thereof from the assembly position to the secured position, is possible in user friendly manner because the securing device 86 and the head part 16 are arranged to be symmetrical. In consequence, the securing device 86 can be inserted into the connecting element receptacle 28 through the insertion opening 34 and also through the insertion opening 38, namely, by leading respectively with the wall 90 or the wall 92. During the process of insertion into the connecting element receptacle 28, the top wall 30 functions as a guide means for the element 88. This makes it easier for a user to accurately insert the securing device 86 into the connecting element receptacle 28.

Figure 2:
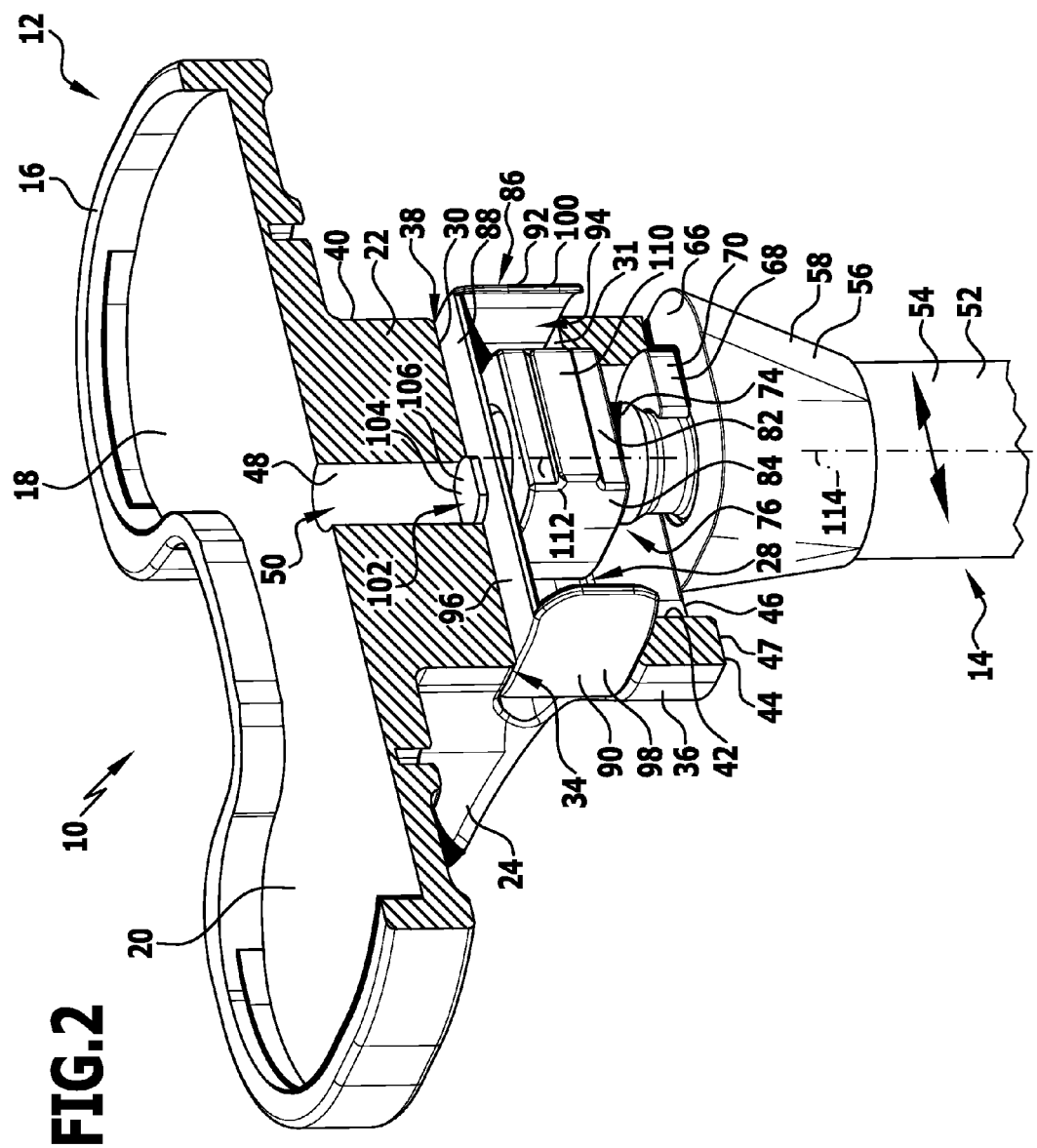
FIG. 2: is a perspective view of the implant along the line 2-2 in FIG. 1 in the form of a partially sectional view wherein the first implant part thereof is connected to the second implant part thereof

Once the securing device 86 has been completely inserted into the connecting element receptacle 28, it adopts its secured position wherein the wall 90 is substantially flush with the lateral side wall section 36 and the wall 92 is substantially flush with the medial side wall section 40 (FIG. 2). If the securing device 86 is inserted into the connecting element receptacle 28 in the reverse manner, then the wall 90 is flush with the medial side wall section 40 and the wall 92 is flush with the lateral side wall section 36.

The dimensions of the walls 90 and 92 are such that the respective insertion openings 34 and 38 are substantially fully closed in the secured position of the securing device 86 so that only a very narrow joining gap is formed between the walls 90 and 92 and the respective side wall sections 36 and 40. This has two different effects: on the one hand the nut 84 is securely held in the connecting element receptacle 28 due to the fact that the insertion openings 34 and 38 are closed and consequently it cannot be moved out of them unintentionally, for which reason the respective walls 90 and 92 are also referred to as securing members 98 and 100 of the securing device 86. On the other hand, this gives rise to the possibility that material located outside the implant 10 cannot enter the connecting element receptacle 28 when the implant 10 is being used in a patient's body. Hereby for example, this may be the bone cement which is utilised for fixing the implant part 12 in the tibia and with respect to which the connecting element receptacle 28 is closed by means of the securing device 86.

The securing device 86 can be locked in the secured position. To this end, it comprises a locking device 102 having a locking member 104 in the form of a projection 106 that projects away from the element 88 in the proximal direction. In the secured position of the securing device 86, the projection 106 can latch in the through hole 48 in the head part 16, whereby the direction of engagement thereof in the through hole 48 is orientated perpendicularly to the direction of insertion of the securing device 86 into the connecting element receptacle 28. The securing device 86 is locked in the secured position in a particularly effective manner in this way.

Provision is not usually made for the securing device 86 to be transferred back from the secured position to the assembly position. Should this nevertheless be desired, a user can gain entry to the through hole 48 from the bearing surface 20 in the distal direction using an appropriate plunger or the like and then subject the projection 106 to a force in the distal direction in order to move it out of engagement with the through hole 48. Thereupon, the securing device 86 can be pushed back out again from the connecting element receptacle 28.

In a variant of the implant 10, provision may be made for the securing device 86 to be held in the connecting element receptacle 28 in the secured position in some other positively-locking manner, or, for it to be held therein in a force-locking manner.

Figure 3:
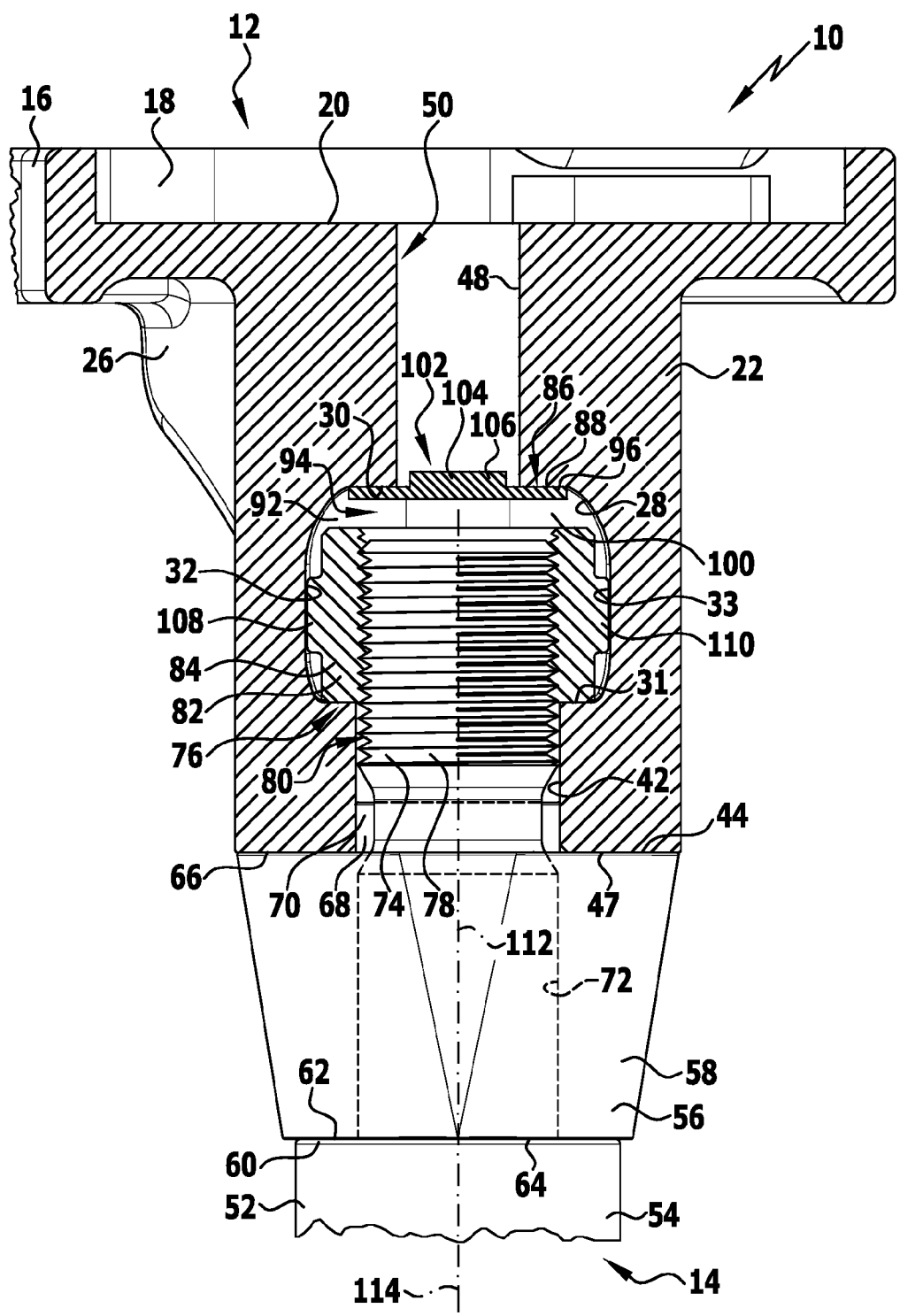
FIG. 3: is a sectional view along the line 3-3 in FIG. 1, wherein the first implant part thereof is connected to the second implant part thereof.

The nut 84 is arranged to be moveable both in the securing receptacle 94 and in the connecting element receptacle 28, wherein, in the latter case in particular, it is mounted in slidable manner and is guided by means of the side walls 32 and 33 of the connecting element receptacle 28. For the purposes of guiding it in the connecting element receptacle 28, the nut 84 comprises a guidance member in the form of a rib 108 which protrudes in the posterior direction and can abut the side wall 32, and also a guidance member in the form of a rib 110 which protrudes in the anterior direction and can abut the side wall 33 (FIG. 3).

Due to this positively-locking fit between the head part 16 and the nut 84 in the posterior-anterior direction, the ribs 108 and 110 simultaneously function as rotation-preventing members which prevent the nut 84 from rotating relative to the head part 16 in the connecting element receptacle 28. It is ensured in this way that, in the secured position of the securing device 86, an axis 112 of the nut 84 is always orientated perpendicularly with respect to the abutment surface 47 for the second implant part 14 so that it can be brought into alignment with an axis 114 of the shaft 54 in a simple manner. This makes it easier for a user to align the shaft 54 relative to the nut 84 and thereby connect the first implant part 12 to the second implant part 14.

As long as the threaded section 78 is not screwed firmly into the nut 84, then, as already mentioned, the shaft 54 together with the collar 58 can be displaced in the lateral-medial direction along the abutment surface 47. This enables the orientation of the second implant part 14 relative to the first implant part 12 to be selected in accord with the needs of the patient when inserting the implant 10 into the body of the patient (FIG. 2). If the threaded section 78 is screwed firmly into the nut 84, then it is no longer possible to have any relative movement between the first implant part 12 and the second implant part 14 (FIG. 3).

The achievement of the invention's object which is obtained in accordance with the invention thus enables the user to handle the implant 10 in a simple manner and permits him to insert the implant 10 smoothly into the body of the patient.

The teachings of the invention can be used not just for the tibia-side part of a knee joint endoprosthesis. It is also possible for the femur-side part of the knee joint endoprosthesis, comprising a femur part and also a femur shaft, to be provided in accordance with the teachings of the invention. Moreover, other types of implant, which are not intended for the formation of a knee joint endoprosthesis, can also be provided in accordance with the teachings of the invention.

What is claimed is:

1. A medical implant, comprising:
a first implant part,
a second implant part,
a connecting device for connecting the first implant part and the second implant part,
said first implant part comprising a connecting element receptacle, in which at least one connecting element of the connecting device is disposable, and
a securing device for securing the at least one connecting element in the connecting element receptacle,
wherein:
the connecting device comprises a first connecting element disposed in the connecting element receptacle in a moveable manner in a secured position of the securing device and a second connecting element disposed on the second implant part,
the connecting element receptacle comprises at least one engagement opening for the second connecting element,
the second connecting element is adapted to be passed through the at least one engagement opening in order to engage with the first connecting element in the connecting element receptacle,
the at least one engagement opening comprises an elongate through hole in a wall region of the first implant part,
the wall region forms an abutment surface for the second implant part, and
the second implant part is displaceable along the abutment surface as long as the first and second connecting elements are not firmly connected to one another.

2. An implant in accordance with claim 1, further comprising an abutment member associated with the first connecting element upon which the first connecting element is placeable for inserting it into the connecting element receptacle.

3. An implant in accordance with claim 1, wherein the securing device comprises at least one securing member for securing the first connecting element in the connecting element receptacle.

4. An implant in accordance with claim 3, wherein the connecting element receptacle has at least one insertion opening for the first connecting element, said insertion opening being completely or substantially completely closeable by means of the at least one securing member.

5. An implant in accordance with claim 4, wherein the at least one insertion opening is formed in a wall section of the first implant part and wherein at least sections of the at least one securing member are flush with the wall section or are substantially flush with the wall section.

6. An implant in accordance with claim 1, wherein the securing device is transferable from an assembly position, in which the first connecting element is adapted to be inserted into the connecting element receptacle, into the secured position in which the first connecting element is secured in the connecting element receptacle by means of the securing device.

7. An implant in accordance with claim 6, wherein the securing device is adapted to be inserted entirely into the connecting element receptacle, said securing device not protruding beyond outer boundaries of the first implant part.

8. An implant in accordance with claim 1, wherein the securing device has a locking device for locking the securing device in the secured position.

9. An implant in accordance with claim 1, wherein the first connecting element is mounted in the connecting element receptacle in a slidable manner in the secured position of the securing device.

10. An implant in accordance with claim 1, wherein the first implant part defines a guide for the first connecting element disposed in the connecting element receptacle.

11. An implant in accordance with claim 1, wherein the first connecting element comprises at least one rotation-preventing member for preventing the first connecting element from rotating relative to the connecting element receptacle.

12. A knee joint endoprosthesis, comprising:
at least one implant, the at least one implant comprising:
   a first implant part,
   a second implant part,
   a connecting device for connecting the first implant part and the second implant part,
   at least said first implant part comprising a connecting element receptacle, in which at least one connecting element of the connecting device is disposable, and
   a securing device for securing the at least one connecting element in the connecting element receptacle,
wherein:
the connecting device comprises a first connecting element disposed in the connecting element receptacle in a moveable manner in a secured position of the securing device and a second connecting element disposed on the second implant part,
the connecting element receptacle comprises at least one engagement opening for the second connecting element,
the second connecting element is adapted to be passed through the at least one engagement opening in order to engage with the first connecting element in the connecting element receptacle,
the at least one engagement opening comprises an elongate through hole in a wall region of the first implant part,
the wall region forms an abutment surface for the second implant part, and
the second implant part is displaceable along the abutment surface as long as the first and second connecting elements are not firmly connected to one another.

13. An implant in accordance with claim 1, wherein the elongate hole is oriented transversely relative to an axis of the first connecting element disposed in the connecting element receptacle.

14. An implant in accordance with claim 1, wherein the abutment surface comprises an abutment flange for the second implant part.

15. An implant in accordance with claim 1, wherein the first connecting element is in the form of a nut adapted to be connected to the second connecting element which is in the formed of a threaded section.

16. An implant in accordance with claim 1, wherein:
the second implant part comprises a shaft and a collar adapted to be placed on the shaft,
the shaft and the collar have respective abutment surfaces, and
a proximal end of the shaft which passes through the collar forms the second connecting element.

17. An implant in accordance with claim 16, wherein the shaft is rotatable with respect to the collar as long as the first and second connecting elements are not firmly connected to one another.

18. An implant in accordance with claim 16, wherein the collar comprises an abutment surface to abut on the abutment surface formed on the wall region.

19. An implant in accordance with claim 18, wherein there is provided on the abutment surface of the collar a rotation-preventing member configured to project into the elongate hole to prevent rotation of the collar with respect to the wall region while allowing the collar to be displaced along the abutment surfaces as long as the first and second connecting elements are not firmly connected to one another.

20. A medical implant, comprising:
a first implant part,
a second implant part,
a connecting device for connecting the first implant part and the second implant part,
at least said first implant part comprising a connecting element receptacle, in which at least one connecting element of the connecting device is disposable, the connecting element receptacle comprising at least one insertion opening for the at least one connecting element; and
a securing device comprising at least one securing member for securing the at least one connecting element in the connecting element receptacle,
wherein:
the securing device comprises an abutment member upon which the at least one connecting element is placeable for insertion into the connecting element receptacle through the at least one insertion opening together with the abutment member; and
the at least one insertion opening is at least partially closeable by means of the at least one securing member.

* * * * *